United States Patent [19]

Luzzana et al.

[11] Patent Number: 5,976,465
[45] Date of Patent: Nov. 2, 1999

[54] APPARATUS AND METHOD FOR THE DETERMINATION OF SUBSTANCES IN SOLUTION SUSPENSION OR EMULSION BY DIFFERENTIAL PH MEASUREMENT

[75] Inventors: Massimo Luzzana; Luigi Rossi Bernardi, both of Milan, Italy

[73] Assignee: Universita Degli Studi Di Milano, Milano, Italy

[21] Appl. No.: 08/838,237

[22] Filed: Apr. 17, 1997

[30] Foreign Application Priority Data

May 2, 1996 [GB] United Kingdom .................... 9609249

[51] Int. Cl.⁶ .................................................. G01N 27/333
[52] U.S. Cl. ...................... 422/82.03; 422/81; 422/82.01; 436/149; 436/163; 436/180; 204/403; 204/416; 204/433
[58] Field of Search .............................. 422/68.1, 79, 81, 422/82.01, 82.03, 104; 436/43, 52, 149, 163, 174, 179, 180; 204/405, 416, 433

[56] References Cited

U.S. PATENT DOCUMENTS

| | | |
|---|---|---|
| 4,353,867 | 10/1982 | Luzzana ..................................... 422/68 |
| 4,361,540 | 11/1982 | Weinberg et al. ......................... 422/68 |
| 4,391,775 | 7/1983 | Huber et al. ............................... 422/68 |
| 4,490,235 | 12/1984 | Calzi ........................................ 204/409 |
| 4,865,992 | 9/1989 | Hach et al. ................................ 436/51 |
| 4,873,057 | 10/1989 | Robertson et al. ........................ 422/75 |
| 5,192,509 | 3/1993 | Surjaatmadja et al. ................... 422/75 |
| 5,580,441 | 12/1996 | Amemiya et al. ....................... 205/789 |

*Primary Examiner*—Long V. Le
*Attorney, Agent, or Firm*—Nixon & Vanderhye, P.C.

[57] ABSTRACT

Analyzers determine the concentration of a test substance by measuring the change of pH in a sample liquid after reaction of the test substance with a reactant. The analyzers have a tube connected between first and second microcapillary pH electrodes. In a first embodiment, the tube functions as a reaction chamber by having a reactant immobilized on a wall of the tubing or confined within the tubing. In a second embodiment, the reactant and test substance are mixed upstream relative to the first and second microcapillary pH electrodes, with the tubing serving as a delay circuit for a kinetic measurement. Output signals of the microcapillary flow-through electrodes are used to determine a change in pH, the change in pH being indicative of the concentration of the test substance.

18 Claims, 5 Drawing Sheets

APPARATUS AND METHOD FOR THE DETERMINATION OF SUBSTANCES IN SOLUTION SUSPENSION OR EMULSION BY DIFFERENTIAL PH MEASUREMENT

BACKGROUND OF THE INVENTION

Differential pH analyzers (Luzzana M., Perrella M., Rossi-Bernardi L. Anal. Biochem. 1971;43:556–563, U.S. Pat. No. 4,353,867 and EP 52718) have been extensively used to measure the concentration of chemicals in various fluids. Indeed, more than 45 papers describing the apparatus and related methods of analysis have appeared in the international literature in the last twenty years.

The essential features of a differential pH analyzer have been described in detail in the original paper and in the patents cited. The apparatus, using appropriately formulated reagents, has been used to determine a variety of substances (such as glucose, urea, creatinine, ethanol, lactate, acetate, ATP, fructose, magnesium) and the activity of several enzymes (i.e., cholinesterase, glucose-6-phosphate dehydrogenase, pyruvate kinase) in the absence or in the presence of inhibitors.

It should be noted that the key analytical equation used in differential pH measurements to calculate $\Delta[H^+]$ (i.e., the number of hydrogen ions, in moles per liter, liberated or absorbed in a chemical reaction involving the analyte to be determined) is given, under appropriate experimental conditions, by:

$$\Delta[H^+]=\beta(pH_{(1)}-pH_{(0)})=\beta\Delta pH \qquad (1)$$

where $\beta$ is the so-called "buffer value", i.e., $\Delta[B^+]/\Delta pH$ of the solution at any given pH and $pH_{(0)}$, $pH_{(1)}$ are the pH values of the solution before and after the chemical reaction of interest has occurred. In this context, pH is equal to $-\log_{10[H^+]}$.

It has been shown in the cited literature that eq. (1) can be used to determine $\Delta[H^+]$ from the known values of $pH_{(1)}$, $pH_{(0)}$ and $\beta$. It should be noted that according to (1), the number of hydrogen ions produced or absorbed in a given reaction, which is directly correlated, through a known chemical reaction, to the amount of analyte present in solution, is proportional to the difference in pH and not to the absolute value of this parameter. In actual practice, the concentration of the substance of interest is obtained by the device described in U.S. Pat. No. 4,353,867 by the slightly more complicated equation:

$$[\text{substance}]=FCAL(\Delta pH_c-\Delta pH_b-\Delta pH_a)=FCAL\,\Delta pH \qquad (2)$$

where FCAL represents a calibration factor which is a combination of $\beta$ and a dilution factor of the sample under analysis, $\Delta pH_c$ represents the total change of pH in solution after a reaction has occurred, $\Delta pH_b$ is the $\Delta pH$ value of the solution after the addition of the reagent(s), but without the sample, and $\Delta pH_a$ is the $\Delta pH$ value indicative of the level of noise and drift of the machine components during the observation time. Since FCAL, $\Delta pH_b$, $\Delta pH_a$ can be determined in separate experiments and by the use of a suitable standard, eq. (2) allows the determination of the concentration of the substance of interest from the calculated value of $\Delta pH$.

It should also be stressed that to avoid in current practice measuring $\beta$ (the buffer value of the solution after the addition of each sample), such a buffer value has to be much higher (50–100 times higher than that of the sample) so that any change in $\beta$ is made practically negligible after such an addition. This, in turn, leads to the necessity of measuring the $\Delta pH$ occurring in a given chemical reaction with an experimental reproducibility of 0.0001 pH units, at least twenty times greater than in the current practice of measuring pH with the already available instrumentation.

The configuration of the apparatus as described in U.S. Pat. No. 4,353,867, and therein shown in FIGS. 1–5, and particularly the simultaneous measurement of the pH difference between two glass pH electrodes respectively filled with a buffer plus sample and buffer plus sample plus a specific reagent(s) to initiate a chemical reaction (typically a small volume of an enzyme) was specially intended to increase the sensitivity and reproducibility of pH measurements In fact, by use of the previously disclosed apparatus and related methods, it has been possible:

a) to zero any unspecific pH drift which may occur (thereby obscuring the measurement of $\Delta pH$) when a biological sample (whole blood, urine, cell suspension and similar solutions or suspensions) is mixed into a buffer of different pH;

b) to minimize the effect on $\Delta pH$ by a change in temperature;

c) to practically zero the difference in junction potential that occurs when a traditionally pH cell made by a glass pH electrode and a reference electrode are immersed respectively into a solution having a standard composition and pH and into a solution having a chemical composition and pH different from the standard.

The practical use of the previously patented apparatus in a variety of analytical problems, although confirming its wide applicability, accuracy and precision, has made clear some of its limitations: the instrument has a weight of no less than 5 kg, it has to be maintained by a trained operator, it requires up to 2–3 ml of reagents for a single determination, especially to assure the complete removal from the electrodes of contamination from the previous cycle of analysis, and, finally, it requires the manual introduction of a precise volume of sample, an operation which may be critical with certain heterogeneous solutions or suspensions. As such, the analyser cannot be uses for the continuous monitoring of an industrial process or chemical parameters of biological and clinical interest in vivo (e.g., urea, creatinine, bicarbonate concentration in an artificial kidney, the determination of glucose in subcutaneous fluids during insulin or glucose perfusion etc.).

DESCRIPTION OF THE INVENTION

SUMMARY

The apparatus according to the present invention (hereinafter named analyzer) substantially comprises:

first means to transfer a suitable buffered solution, second means to transfer a sample liquid containing a substance to be determined, said first means bringing said buffer in contact with said substance to be determined to give a buffered sample liquid, third means to deliver a liquid containing a reactant;

a reaction chamber wherein said buffered sample liquid and said liquid containing a reactant come into contact, whereby a reaction mixture is formed, causing a pH change in solution;

a first and a second microcapillary pH electrodes;

means to regulate the temperature of said first and said second pH electrodes;

fourth means to deliver said reaction mixture to said first pH electrode, said means comprising means to bring the temperature of said reaction mixture to the same temperature of said first pH electrode, and being at machine ground potential;

fifth means to deliver said reaction mixture to said second pH electrode;

electronic means for processing pH measurements made by said first and second pH electrodes and producing a visual display of the concentration of said substance to be determined.

According to the configuration of the hydraulic circuit, the reaction chamber may be placed either before the first pH electrode or between the first and second pH electrode.

In case the reaction chamber is placed between the pH electrodes, the chamber may consist of a tubing of adeguate lenght and containing a suitable reactant, for example an enzyme or a chemical, that will react with the buffered sample solution thus causing a change of pH.

In the other case, in which the reaction chamber is placed before the first pH electrode, said chamber shall be constructed in such a way to receive the buffered sample liquid and the reactant and to deliver the reaction mixture to the first pH electrode.

Means to transfer and deliver liquids are well known in the art and the skilled person will be able to select then in the most appropriate manner. Examples of said means are pumps, such as microperistaltic pumps.

A sample liquid may be delivered with suitable sampling devices either in continous or batch mode. In case of heterogeneous liquids, such as emulsions or suspensions, the present invention provides in a preferred embodiment a microdialysis probe.

The analyzer shall comprise suitable accessory means, such as flow regulating devices, means to minimize stagnant layers of liquid along the walls of the fluidic connections.

Different configurations of the analyzer of the present invention may be made.

In a first configuration, the analyzer comprises:

a block made of metal or another heat-conducting material in which two micro pH glass electrodes are located, said two electrodes being connected together, in parallel, by a piece of small diameter tubing of various lengths which may contain an immobilized enzyme(s) or another suitable chemical to cause the chemical reaction(s) of interest;

said thermal block and the liquid flowing into the two pH electrodes being connected to a common ground, whereas the two electrode outlets are connected to a differential amplifier circuit associated with a measuring device;

a heat conducting tubing, connected to electrical ground, inserted in the hydraulic circuit, between the sample and first measuring electrode so to heat a sample solution to electrode temperature;

a buffer whose known composition can be varied to ensure the occurrence of a chemical reaction in conjunction with a chemical substance, for example an enzyme immobilized or confined in the tubing connecting the two pH electrodes;

electronic means to convert pH electrode potentials into pH values, to program the functioning of the apparatus and to calculate, print or store, according to a known stoichiometry and related equations, the concentration of the substance(s) of interest;

microperistaltic pump(s) or other suitable device(s) to move, in a series of microbore tubings and through the two measuring pH electrodes, the solution under analysis;

a microdialysis tubing to sample, by diffusion through a dialysis membrane, a definite amount of the substance to be determined contained at a known concentration in an outside liquid or in an unknown concentration in a sample to be analyzed.

Preferably, the analyzer also comprises:

mechanical means to change in an oscillatory mode the flow rate of the liquid in the measuring pH capillary electrodes, inside the microdialysis probe and in the tubing connecting the various parts of the apparatus so to renew the stagnant layer of liquid around the inner walls of the circuit.

In a second configuration, the analyzer, having a similar thermal block and two micro pH glass electrodes connected by a tubing of variable length to provide a time difference between the solution continuously flowing through first electrode and the same solution flowing through second electrode, comprises:

two microperistaltic pumps, the first pump delivering to a mixing chamber a buffer of known suitable composition, or the same buffer containing a standard concentration of the substance to be determined, or a solution containing an unknown concentration of the substance to be determined and the second pump delivering to a mixing chamber a buffer containing a chemical substance(s) such as an enzyme(s) to start the chemical reaction;

a mixing chamber to effectively mix two fluids, which are continuously delivered to said mixing chamber by the two peristaltic pumps;

mechanical means to oscillate the tubing coming from the mixing chamber in order to minimize the stagnant layer of liquid on the inner wall of the hydraulic circuit and of the two measuring pH electrodes;

a small diameter tubing to deliver the mixed fluid into the two capillary electrodes, arranged in series and connected together through a delay tubing.

BRIEF DESCRIPTION OF THE DRAWINGS

The invention shall be illustrated in detail also by means of Figures and examples. In the Figures.

DETAILED DESCRIPTION OF THE INVENTION

Figure 1:
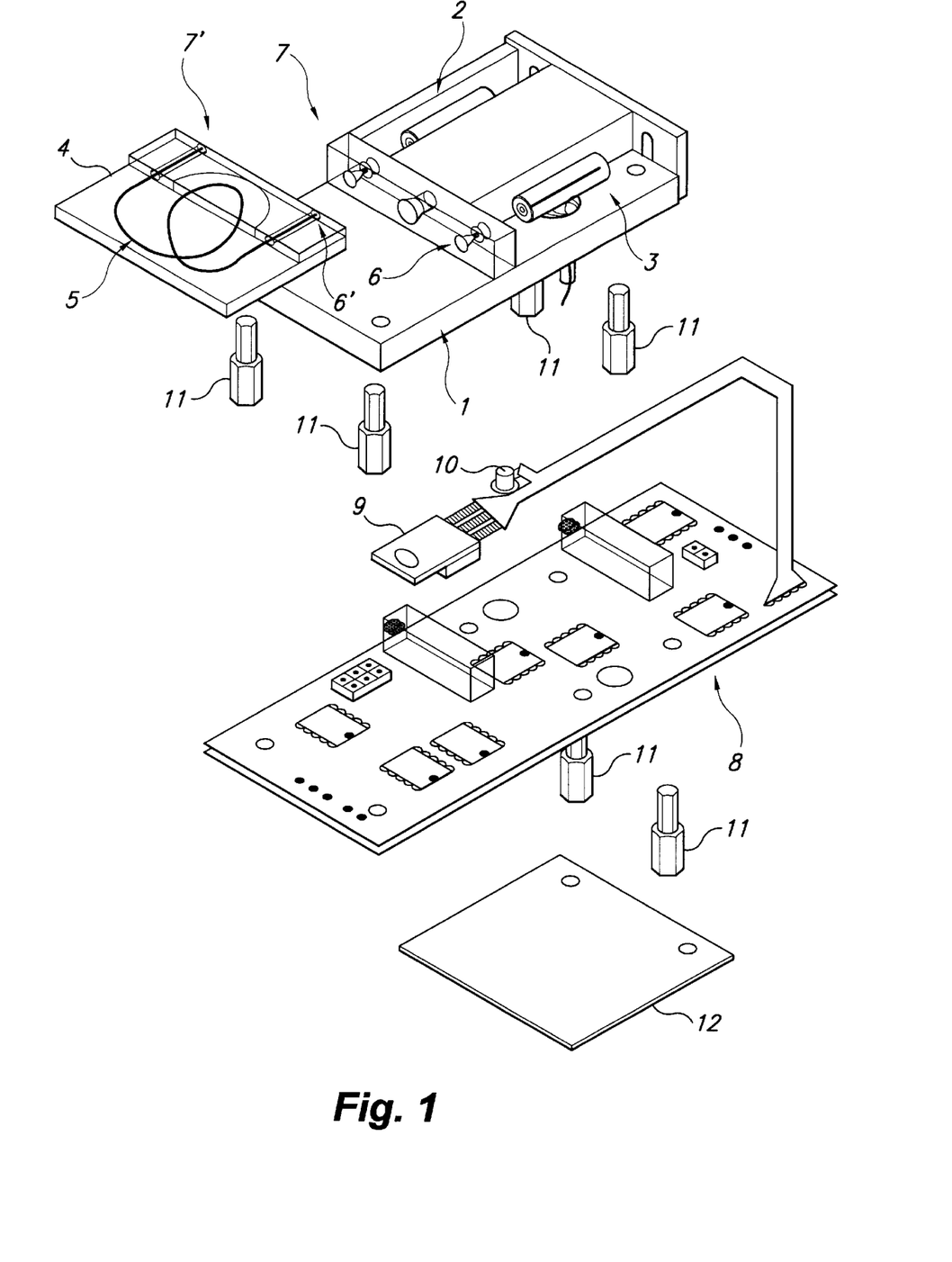
FIG. 1 shows of the apparatus according to the present invention, in particular the microcapillary pH electrode assembly and the electronic control parts.

FIG. 1 shows the measuring and electronic control parts of the analyzer object of the present invention. 1 is a thermal block made of a material with large heat-transferring capacity, where two microcapillary pH electrodes, 2 and 3, are located. The electrodes have an inner volume of about 4 microliters. 4 is an optionally removable block which holds a capillary tubing, 5, which can be made of various materials, such as Teflon, polyether ether ketone (peek), glass and others with a typical inner diameter of 0.2–0.4 mm and variable total length (50–300 mm, as needed). The capillary tubing may contain, immobilized on its wall or confined therein, according to the well-known art (Schmid R. D. (Ed.), Flow injection analysis (FIA) based on enzymes or antibodies. GBF Monographs, vol. 14, WCH, Weinheim, 1991), an enzyme or a chemical substance able to initiate a given chemical reaction. Block 4 can be easily interchanged manually with another similar block holding capillary tubing with a different enzyme or a suitable chemical immobilized therein. The two electrode inlets 6 and 7 are symmetrically positioned with respect to the outlets 6' and 7' of the capillary tubing. When block 4 is pushed into block 1, inlets 6 and 7 form a leak-tight connection with 6' and 7'. 8 is a printed electronic circuit board designed and built according to known principles to operate the apparatus according to a program. 9 is a heat-dissipating device which in the assembled apparatus is attached to block 1, to regulate its temperature. 10 is a temperature sensory device also to be attached to block 1. 11 is the nuts which hold blocks 1 and 8 together. 12 is a protection shield for the glass electrode terminals. It is essential that the temperature of the solution flowing from the sample into the first measuring electrode be brought to the same temperature of said electrode. This is accomplished by flowing solution through a piece of metal capillary tubing of suitable length (not shown in FIG. 1 or 2) in thermal contact with the thermal block. This capillary is also used for grounding the solution.

Figure 2:
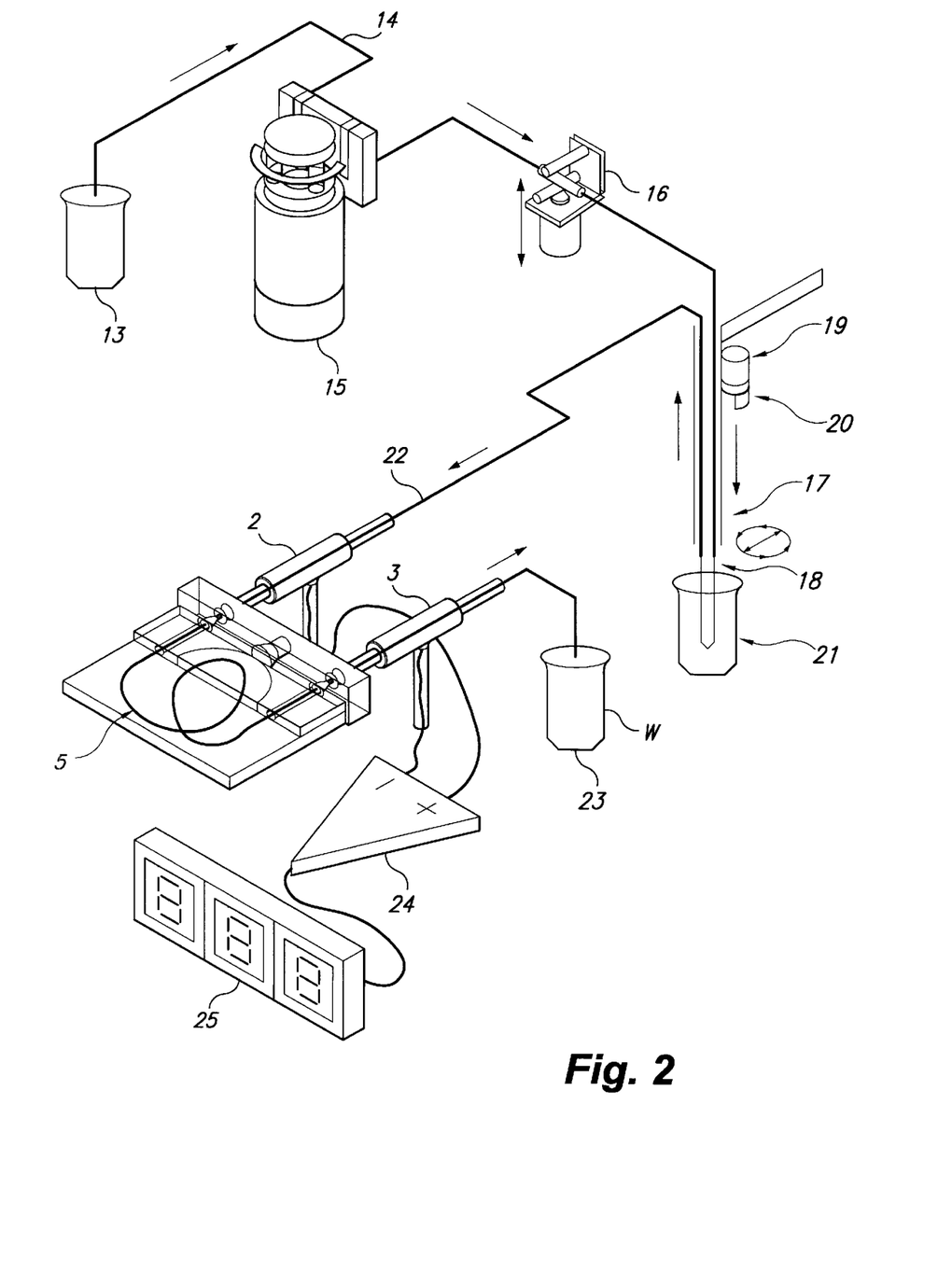
FIG. 2 shows a first embodiment of the hydraulic circuit of the apparatus.

FIG. 2 shows a preferred, but not exclusive configuration of the hydraulic circuit which is responsible for delivering to the two pH electrodes a suitable solution. 13 is a container to hold such a solution, usually consisting of an aqueous buffer solution of a suitable composition. The solution from 13 is moved through the various parts of the hydraulic circuit, connected together by 0.2–0.4 mm inner diameter capillary tubing, 14, made of Teflon, silicone, peek and the like by the action of a microperistaltic pump, 15. 16 is an electrical pinch valve arrangement which induces in the capillary tubing rapid cycles of pressure changes to "instantaneously" change the flow rate of liquid flowing into the capillary tubing and through the various parts of the apparatus. The action of this device is to minimize the formation of a stagnant layer of liquid on the walls of the various components of the circuit. 17 is a microdialysis probe holding a microdialysis fiber, 18 (obtained from Hospal-Dasko, Modena, Italy), connected in series with tubing 14. 19 is a micromotor holding and rotating an eccentric part, 20, which vibrates the microdialysis probe into the liquid contained in 21. The solution contained in 21 may be a standard containing a known concentration of the substance whose concentration has to be determined or an unknown. 22 is the inlet to the first electrode, 2 (described in FIG. 1), leading to loop 5 and then to electrode 3 and from there to a waste container, 23. 24 is a schematic representation of a differential pH amplifier which is a component of the printed circuit board 8 (FIG. 1), to which the electrical output of pH electrodes 2 and 3 are connected. 25 is a device suitable to monitor the differential electrical output of the two electrodes and calculate according to a known formula the concentration of the substance of interest. The microdialysis probe 17 can be arranged according to several alternative configurations, according to the art already known to people working in the microdialysis field. For instance, the microdialysis fiber can be surrounded by a small-diameter tubing into which a fluid containing a diffusible substance, whose concentration has to be determined, is continuously circulated. Such a fluid may be blood or an electrolyte solution coming from an extracorporeal dialysis machine, a cell suspension coming from a fermentation vessel, or other solutions or suspensions.

Figure 3:
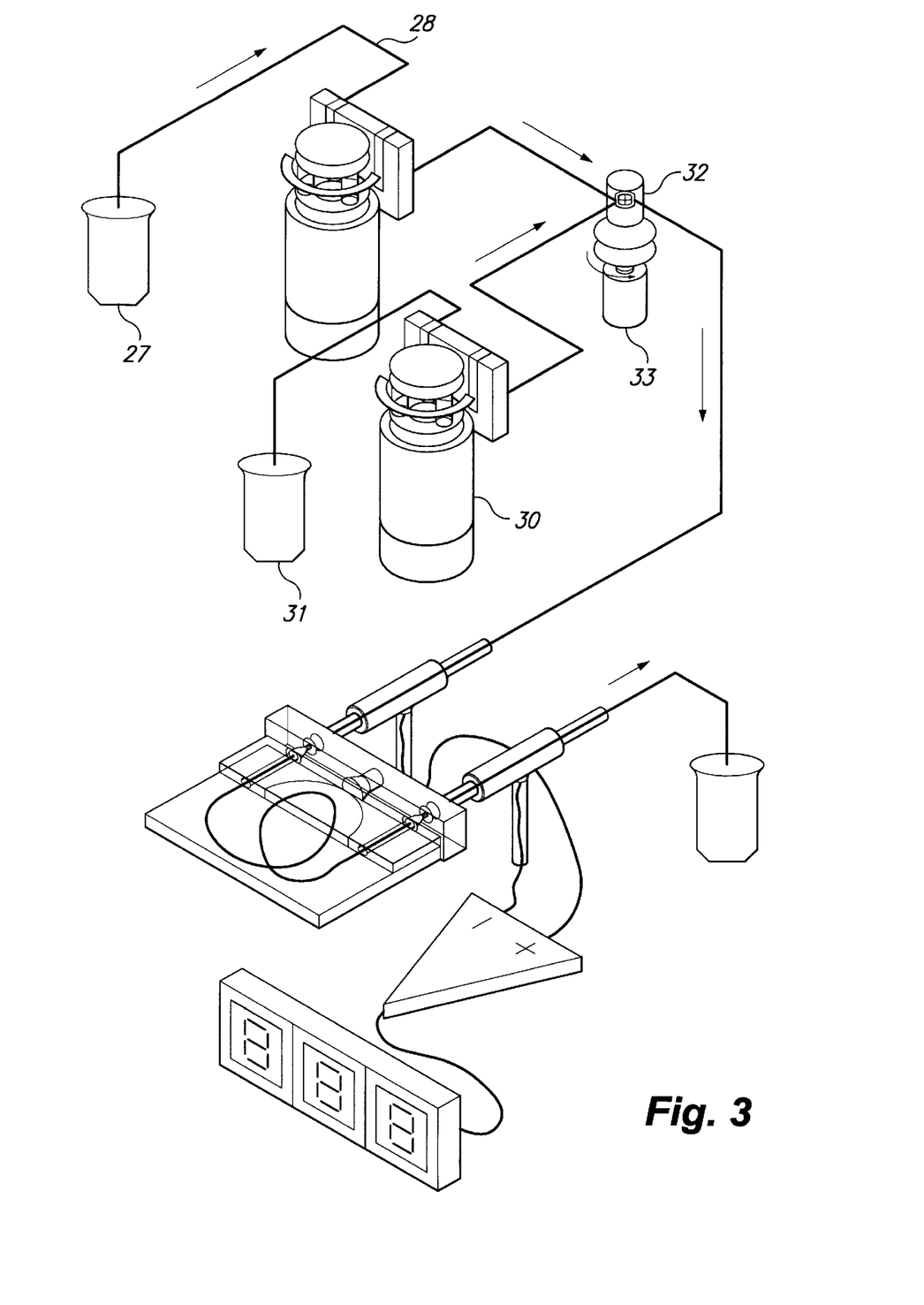
FIG. 3 shows a second embodiment of the hydraulic circuit of the apparatus.

FIG. 3 shows an alternative configuration of the instrument disclosed in FIG. 2. 27 is a suitable reservoir containing the substance whose concentration has to be determined. It is intended that such a solution may be contained in the reservoir or may be continuously sampled or fed into the capillary tubing 28. 29 and 30 are two microperistaltic pumps similar to pump 15 (FIG. 2). Pump 30 samples a suitable liquid from 31 or other containers or outlets. 32 is a mixing chamber containing a small magnet which is moved by micromotor 33, holding a magnet so that a mixing action is magnetically induced into 32. The content of capillary tubing 28 can rapidly be oscillated by adding a pinch valve such as 16 (FIG. 2) (not shown in FIG. 3), having on the stagnant layer of liquid along the walls of the various parts of the apparatus a similar effect as previously described. All other parts represented in FIG. 3 have similar meaning, as explained in FIG. 2. Principles of operation of the new apparatus The operation of the apparatus will be described with reference to FIGS. 1 and 2. The dialysis probe, i.e., a small length of dialysis tubing made of a semi-permeable membrane through which chemical substances of a suitable molecular weight can diffuse, is first immersed into a standard solution, where the substance to be measured, T, is contained at a known concentration, i.e., moles/liter, [T]. The microperistaltic pump 15 continuously circulates a buffer contained in 13 (FIG. 1) through the hydraulic circuit shown in FIG. 1 at a rate determined by the microperistaltic pump 15, which is regulated through the action of the electronic part of the apparatus. The composition of the buffer is made to contain all the chemical components necessary to react with the substance to be determined, except for a final reagent(s) which is chemically or physically confined to the inner wall of tubing 5. The substance, which as said has a known concentration [T], diffuses from the liquid contained in 21 into the solution flowing through the dialysis probe, and the mixture is carried to inlet 2 of the first capillary pH electrode and from there into tubing 5 and capillary electrode 3. Upon continuously flowing (and,. if necessary, after being stopped in 5 for a definite period of time) through tubing 5, which contains a given chemical (e.g. an enzyme) immobilized in its wall, a known reaction occurs, liberating or absorbing a certain amount of hydrogen ions. Upon reaction with the components of the solution, a change in [$H^+$] concentration will occur in 5. Such a change will be monitored by the second electrode 3. The two different values of [$H^+$], before (electrode 2) and after (electrode 3) a given reaction has occurred, are recorded as a difference in the electrical potential between the two electrodes by the electronic measuring system 24 and 25. A value of $\Delta pH = \Delta pH_T$ arising from the two pH electrodes is calculated according to a well-known previous art of electrical measurements.

The operation is repeated by transferring probe 18 (FIG. 1) from T to S, which is another solution containing the same substance at an unknown concentration, all other conditions of the operation being the same as before. In this case, a new value of $\Delta pH = \Delta pH_S$ will be recorded. Under appropriate experimental conditions, it can be shown that:

$$[S] = [T] \times \Delta pH_S / \Delta pH_T \qquad (3)$$

Since [T] is known and $\Delta pH_S$ and $\Delta pH_T$ are measured, [S] can be obtained by simple calculations. such calculations are made according to standard programs by the electronic components of the apparatus and can be visualized, printed or stored in the memory of the electronic circuit.

It should be made clear that to obtain meaningful results it is not essential that the diffusion process in the microdialysis tubing and the chemical reaction occurring in 5 reach final equilibrium. In fact, according to the well-known previous art of continuous flow analysis, proper functioning of the analytical system requires only the attainment of a steady state value for the physical and chemical processes involved.

A second preferred, but not exclusive, arrangement of the electrodes and the fluid circuit (which is necessary to deliver to the two capillary pH electrodes respectively a standard or a sample solution) is shown in FIG. 3. In this configuration, two peristaltic pumps (instead of one, as shown in FIG. 1) deliver to mixing chamber 32 through two capillary tubes the solutions respectively contained in 27 and 31. 27 may contain a solution of a given composition (buffer), a buffer plus a substance in a known concentration [T], or a buffer plus the same substance in an unknown concentration. 31 may contain a chemical substance (for example, an enzyme) dissolved in a buffer mixture of a given chemical composition. To ensure a better mixing, the mixing chamber 32 contains a small magnet magnetically coupled to another magnet rotated by micromotor 33. Upon mixing in 32, a known reaction between the chemical components of the solutions coming from reservoir 27 and 31 begins. The solution continuously flows from 32 into the first and second pH electrodes through tubing 5, which, in a particular case, may simply act as a delay circuit to allow the measurement of pH by the two pH electrodes at different times from the beginning of the reaction in 32. In short, in this configuration the first electrode 2 "sees" the chemical reaction under study at time 1 from its start, whereas the second electrode 3 "sees" the same reaction after a delay time $\Delta T$, which is determined by the volume of the delay loop 5 and the flow rate of ligand into the system. By an appropriate choice of such a flow rate and of the concentration of reactants, the ratio $\Delta pH/\Delta t = R$ can be suitable chosen and measured. This ratio, when determined under appropriate experimental conditions, for the case respectively of a standard or of a sample containing the substance whose concentration has to be determined, allows the calculation of the unknown concentration of S, [S], according to $$[S]=[T] R_S/R_T \quad (4)$$

Since $R_S(=\Delta pH_S/\Delta t)$ and $R_T(=\Delta pH_T/\Delta t)$, respectively for a standard or an unknown sample, are measured and [T] is known, the concentration [S] can be obtained through (4). A mixing arrangement: as shown in FIG. 1, 16, can be added to the apparatus to minimize the presence of stagnant layers of liquid in tubing 5 and in the measuring pH electrodes. This second, alternative version of the apparatus object of the present invention is particularly useful for the determination of an enzymatic activity or for the determination of an unknown analyte using a kinetic approach, according to the previously known art of kinetic analysis (Henry R. J. Clinical Chemistry: Principles and Technics. Hoeber medical, Division of Harper and Row, 1966.).

Application of the apparatus for determination of the concentration of chemical substances The apparatus described in the present application may be applied to a variety of analytical problems. In fact, a large number of chemical reactions occurs with the absorption or liberation of hydrogen ions.

The apparatus in its several possible versions, of which only two have been herein described in detail, is best used for the determination of substances dissolved in heterogeneous solutions or suspensions, i.e., in turbid or heavily colored samples such as whole blood, urine, milk, wine, which are not amenable for their nature to analysis by other standard methods such as colorimetry and fluorometry. Another preferred use of the new instrument is in the continuous determination of substances in a variety of experimental conditions such as in the monitoring of effluents from an analytical or industrial process or of biological fluids in vivo.

To demonstrate the practical utility of the new invention, the results of two typical experiments on the determination of urea in milk and of bicarbonate in the ultrafiltrate from an extracorporeal dialysis machine are reported.

EXAMPLE 1

Four cow milk samples containing urea in the concentration range of 20–50 mg/dL were analyzed by the method accepted by the French Association for Normalization (AFNOR NF V04-217). The method involves precipitation of the proteins of milk, transformation of urea into ammonia by urease, and determination of ammonia produced in this reaction by the use of the enzyme glutamate dehydrogenase and NADH, whereby NADH is oxidized to $NAD^+$ and the change in absorbance is measured at 340 nm by a spectrophotometer. The concentration of urea in the same samples of whole milk was also measured without any previous treatment of the sample by the apparatus according to the present invention shown in FIG. 1. In this case, the composition of the buffer contained in 13 (FIG. 1) was phosphate, at a total concentration of 40 mM/l, KCl at 100 mM/l, $MgCl_2$ at 5 mM/l, $NaN_3$ at 1 g/l, and detergent at 30 g/l, pH 7.3. The microdialysis fiber was AN69 by Hospal-Dasko, made of polyacrylonitrile, 0.22 mm ID, 0.32 mm OD, 50 mm total length. The reactor tubing 5 (FIG. 1) was 100 mm long, 0.3 mm D, and loaded with 20 U of urease. The buffer flow rate in the hydraulic circuit was 400 μl/min.

The measurements with the apparatus shown in FIG. 1 have been performed as follows: a: the dialysis probe is immersed in a standard aqueous solution (i.e., urea in a concentration of 20 mM/l) and a first reading of $\Delta pH$ ($\Delta pH_1$) is obtained after 40 sec; b) the dialysis probe is immersed in an aqueous solution as in a) but without urea for 40 sec and a zero $\Delta pH$ reading is taken ($\Delta pH_2$); c) the dialysis probe is immersed in the whole milk sample for 40 sec and a third $\Delta pH$ ($\Delta pH_3$) is obtained.

[S], the urea concentration of the whole milk sample, is calculated according to $$[S]=[T]\times(\Delta pH_3-\Delta pH_2)/(\Delta pH_1-\Delta pH_2)=[T]\times\Delta pH_S/\Delta pH_T \quad (5)$$

$\Delta pH_2$ is a small calibration factor, usually constant with time, and is indicative of the level of noise and drift of the machine components during the observation.

The results of urea concentration determinations by the two different methods are as follows:

| | Urea concentration (in mg/dl) by the two methods | | |
|---|---|---|---|
| Sample | AFNOR method (1) | New apparatus (2) | Δ (1-2) |
| 1 | 21.2 | 21.4 | −0.2 |
| 2 | 28.0 | 26.9 | +1.1 |
| 3 | 37.5 | 37.0 | +0.5 |
| 4 | 48.5 | 49.6 | −1.1 |

The reported differences between the two methods, of the order of 2%, are well within the accepted experimental error of determination by the standard AFNOR method.

It should be noted that the determination of urea concentration in whole milk by the new apparatus is much faster, does not require precise chemical manipulation of the sample such as pipetting, precipitation, centrifugation or other operations that usually require a laboratory environment and as such can be used by a relatively unskilled operator in field operations. It also requires a smaller volume of expensive reagents and, finally, requires a minimum time compared to that of the standard method of analysis.

EXAMPLE 2

The results of a second test of the performance and usefulness of the apparatus herein described in FIG. 2 were as follows. Four different solutions containing bicarbonate at 0, 20, 30 and 40 mM/l were sampled from 31 by the microperistaltic pump 30 and mixed in the mixing chamber 32 with a buffer solution delivered by microperistaltic pump 15 having the following composition: 20 mM phosphate, 100 mM KCl, 1 g/l $NaN_3$, 1 g/l detergent, 5 mM $MgCl_2$, 10 mg/l acetazolamide, pH 6.4. The flow rate from 15 into the mixing chamber was 60 μl/min, and flow rate from 30 into the mixing chamber was 120 μl/min. The reactor delay loop 15 had a volume of 30 μl corresponding to a 10-sec-delay interval between electrode 2 and electrode 3 when the total flow in the measuring circuit was 180 μl/min.

Figure 4:
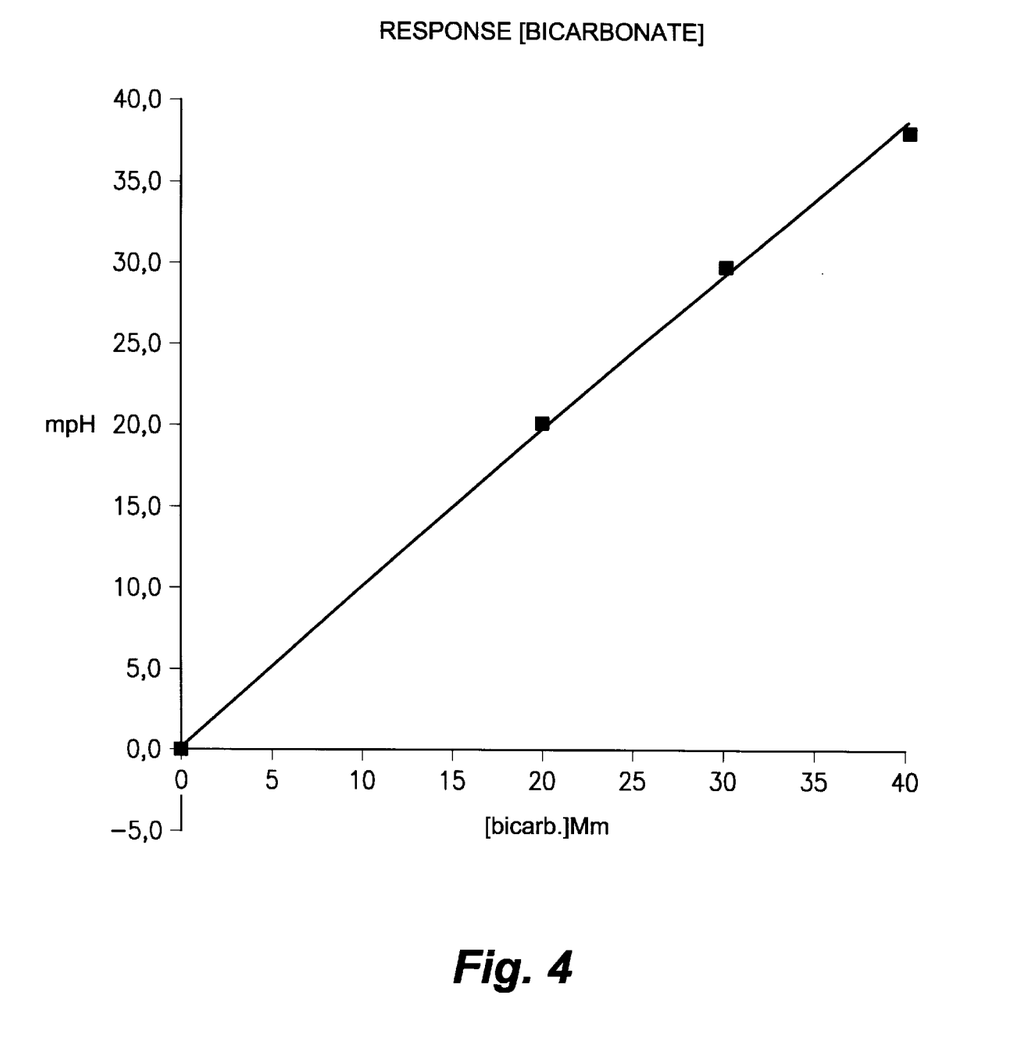
FIG. 4 shows a calibration curve for the determination of bicarbonate in an unknown solution.
Figure 5:
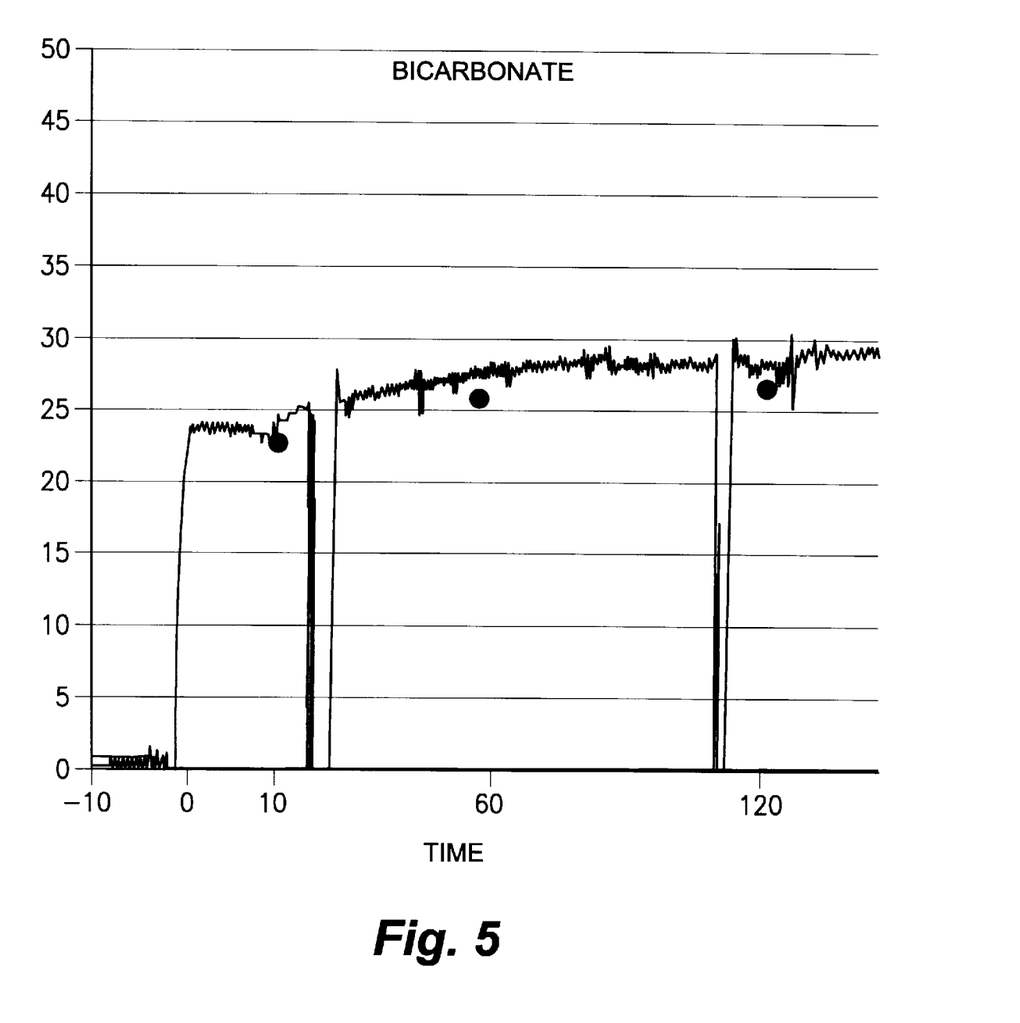
FIG. 5 shows a continuous bicarbonate determination in the effluent of an extracorporeal dialysis machine.

Upon mixing of the two solutions in 32, the reaction $$H^+ + HCO_3^- \longleftrightarrow H_2CO_3 \longleftrightarrow CO_2 + H_2O$$

will proceed to equilibrium from the left to the right with the simultaneous absorption of hydrogen ions (and increase in pH). By plotting the change in pH, ΔpH, measured in the differential pH cell versus the standard bicarbonate concentration, the linear relationship of FIG. 4 was obtained and used as a calibration for the determination of bicarbonate in an unknown solution. FIG. 5 shows an actual continuous bicarbonate determination in the effluent of an extracorporeal dialysis machine over a period of 3 hr. The points shown on the same graph represent bicarbonate concentration in samples obtained from the same solution, as individually sampled and analyzed according to the known art of measurement by a standard method. The correspondence between the two methods of analysis was found to be within ±3% of the actual value, as measured by the aforementioned standard method. This range of error is well within the clinical significance of the measurement itself.

The use of a two pH electrode analytical module in the newly disclosed configuration and mode of operation requires a careful consideration of blank factors which are of a different nature from those previously described in U.S. Pat. No. 4,353,867.

In fact, any aspecific pH change (not arising from the specific reaction of a substance) with a time span to differently affect the measurement of pH respectively by the first and second electrode (which, as may be recalled, are arranged in series and will record the pH of the flowing solution at two different times) will introduce an error in the measurement of the true ΔpH of the reaction.

This case is typically represented by the sample solution containing a different amount of total $CO_2$ with respect to that contained in the standard solution, a situation which may well occur during the determination of a substance contained in the plasma of a person (usually containing a total $CO_2$ of around 25 mM/l) or in other similar cases involving a biological fluid.

In this circumstance, the sample will contain a certain amount of $CO_2$, whereas the standard solution will not. In the first case, $CO_2$ will diffuse through the dialysis probe into the buffer solution and the different $CO_2$ forms will equilibrate with each other to reach a new equilibrium according to the well known reactions:

$$CO_2 + H_2O \longleftrightarrow H_2CO_3 \longleftrightarrow H^+ + HCO_3^- \text{ and}$$

$$HCO_3^- \longleftrightarrow CO_3^{--} + H^+$$

This will produce a change in pH which, if occurring to a different extent at the first pH electrode compared with the second pH electrode (as explained, the measurement of pH by the two pH electrodes is not simultaneous since the electrodes are arranged in parallel) will produce a ΔpH value which will add to or subtract from the ΔpH value produced by the reaction under study.

This blank effect can be easily minimized 1) by making sure that any aspecific reaction will reach equilibrium before the solution reaches the inlet of the first pH capillary electrode. For instance, for the most common case of the hydration-dehydration reaction of $CO_2$, by adding to the buffer a small amount of the enzyme carbonic anhydrase, a powerful catalyst of this reaction; 2) by choosing an appropriate buffer value of the solution flowing through the dialysis probe and the electrodes so that the effect of diffusion in different amounts of buffering substances of low molecular weight respectively from the sample and for the standard is made negligible. If required, such blank effects, usually negligible, can be precisely determined by substituting reaction loop 5 (FIG. 1) with a loop of exactly the same length and volume without an immobilized chemical or enzyme.

From the previous description of the present invention and its mode of operation, it is apparent that substantial advantages over the previously described art can be achieved by the use of the new invention since:

a) the entire apparatus consisting of a small metal block containing two micro pH electrodes, a reactor or a delay line and one (or two) microperistaltic pumps has a total weight of about 350 g, with physical dimensions of 10 (l), 15 (h) and 6 (s) cm, it can be powered by a battery with one day total autonomy. It can thus find useful field use;

b) no precise dispensing of a known volume of a sample or standard solution into a definite volume of a reagent solution is required, thus eliminating the manual intervention of an operator;

c) no precise dispensing of a substance (for instance, an enzyme) to specifically initiate a chemical reaction is required, since such a substance is conveniently chemically immobilized or physically confined in a tube—the reactor—this allowing the repeated, continuous determination of the concentration of the unknown substance;

d) the reactor, whose life of operation may be several days, can be easily interchanged by a simple manual operation with another reactor containing another different chemical substance specific for another reaction, thus allowing the determination of a variety of analytes. The simple operation that is required to change the reactor is also useful when the life span of the reactor itself has expired;

e) adoption of a slightly changed configuration of the microdialysis probe, in which the dialysis tube is surrounded by another tubing into which a liquid containing the substance whose concentration is required is continuously flowing, makes possible the continuous monitoring of a substance in an industrial process or of analytes in the biological fluids of a patient or an animal (e.g., glucose or lactate concentration of blood or of subcutaneous fluids, urea, creatinine or bicarbonate concentration of solutions from an extracorporeal dialysis machine during an in vivo dialysis operation and the like;

f) the cost of the instrument is drastically lower than that of other analytical apparatuses giving similar performance in accuracy and precision in the determination of the same substances;

g) the use of an automatic sampling device coupled with the two micro pH glass capillary electrodes considerably reduces the volume of costly reagents (such as NAD, $NAD^+$, ATP), enzymes or the like, which must be used in the present art of analytical chemistry, clinical chemistry, and analytical biochemistry;

h) contamination or poisoning of the electrodes or the reactor surface by proteins such as enzymes and other high molecular weight components, which may be contained in the sample under analysis (which may be blood, milk, wine, urine, fermentation solutions, cell suspension, etc.) is avoided by the adoption of a microdialysis sampling membrane, separating standard and sample solutions from the fluid contained in the apparatus. The presence of such a membrane also reduces the volume of liquid required to eliminate contamination from a previous analytical cycle, saving costly reagents and thus allowing the monitoring of the change in concentration of the substance under analysis with a considerable faster response time. Although this invention has been described as having two preferred designs and features, it is capable of further modifications. This application is thus intended to cover any variations, uses or adaptations of the invention following the general principles thereof and including such departures from the present disclosure as come within known or customary practice in the art to which this invention pertains and as may be applied to the main features of the invention heretofore set forth and fall within the scope of this invention or thee limits of the claims.

We claim:

1. An analyzer for the determination of the concentration of a substance in a sample liquid, by means of the measurement of a change of pH in said sample liquid after reaction of said substance with a reactant, said analyzer comprising:

first means to transfer a buffered solution, second means to transfer said sample liquid containing said substance to be determined, said first means bringing said buffer in contact with said substance to be determined to give a buffered sample liquid, third means to deliver a reactant;

a reaction chamber wherein said buffered sample liquid and said reactant come into contacts whereby a reaction mixture is formed, causing a pH change in solution;

a first and a second microcapillary flow-through pH electrodes;

means to regulate the temperature of said first and second pH electrodes, fourth means to pump said reaction mixture and to bring the temperature of said reaction mixture to the same temperature of said first pH electrode, said fourth means being at ground potential;

fifth means to deliver said reaction mixture to said second pH electrode;

electronic means for processing pH measurements made by said first and second pH electrodes and producing a visual display of the concentration of said substance to be determined;

wherein said reaction chamber comprises a tubing located between said first and second pH electrodes.

2. An analyzer according to claim 1, wherein said reaction chamber consists of said tubing containing an enzyme immobilized on its wall or confined therein.

3. An analyzer according to claim 1, wherein said second means comprise a microdialysis probe.

4. An analyzer according to claim 3, wherein said first means comprises a microperistaltic pump connected with said microdialysis probe.

5. An analyzer according to claim 1, wherein a flow regulating device is placed between a microperistaltic pump and a microdialysis probe.

6. An analyzer according to claim 3, comprising means to supply said sample liquid into said microdialysis probe.

7. An analyzer according to claim 1, wherein said reaction chamber further comprises a mixing chamber, placed before said first pH electrode.

8. An analyzer according to claim 7, wherein said first means comprise a microperistaltic pump connected to said mixing chamber, said second means comprise a second microperistaltic pump connected to said mixing chamber, said chamber having a common outlet connected to said fourth means to deliver said reaction mixture to said first pH electrode.

9. An analyzer according to claim 8, wherein said common outlet of said mixing chamber and said first electrode are connected by tubings.

10. An analyzer according to claim 1 comprising at least one flow regulating device.

11. An analyzer according to claim 1 comprising means to minimize stagnant layers of liquid along the walls of any one of the first means second means third means and fourth means.

12. An analyzer according to claim 1 comprising devices for supplying said buffer solution, said sample liquid, said reactant either in continuous or batch mode.

13. An analyzer to measure the concentration of a substance in solution based on the determination of the change in pH upon a specific chemical reaction, said analyzer comprising:

a thermal block in which two micro pH glass electrodes are located, said two electrodes being connected together, in parallel, by a piece of tubing which contains an immobilized enzyme to cause the chemical reactions of interest;

said thermal block and a liquid flowing into the two pH electrodes being connected to a common ground, whereas the two electrode outlets are connected to a differential amplifier circuit associated with a measuring device;

a heat conducting tubing, connected to electrical ground, inserted between a sample and first measuring electrode so to heat a sample solution to electrode temperature;

a buffer whose known composition can be varied to ensure a chemical reaction in conjunction with a chemical substance;

electronic means to convert pH electrode potentials into pH values, and to calculate, print or store, according to a known stoichiometry and related equations, the concentration of the substance in solution;

a device for moving, in a series of microbore tubings and through the two measuring pH electrodes, the solution under analysis;

a microdialysis tubing comprising a dialysis membrane through which the substance to be determined diffuses.

14. An analyzer according to claim 13 including:

mechanical means to oscillate the microdialysis tubing into a sample or in a standard solution, in order to minimize a stagnant layer of liquid on the outside of the dialysis membrane.

15. An analyzer according claim 13 including:

mechanical means to change in an oscillatory mode the flow rate of the liquid in the measuring pH capillary electrodes and inside the microdialysis probe.

16. An analyzer according to claim 13 wherein the thermal block and two micro pH glass electrodes are connected by a tubing to provide a time difference between the solution continuously flowing through first electrode and the same solution flowing through second electrode, comprising:

two microperistaltic pumps, the first pump delivering to a mixing chamber a buffer of known composition, or the same buffer containing a standard concentration of the substance to be determined, or a solution containing an unknown concentration of the substance to be determined and the second pump delivering to the mixing chamber a buffer containing a chemical substance to start the chemical reaction;

a mixing chamber to effectively mix two fluids, which are continuously delivered to said mixing chamber by the two peristaltic pumps;

mechanical means to oscillate the tubing coming from the mixing chamber in order to minimize the stagnant layer of liquid on the inner wall of the hydraulic circuit and of the two measuring pH electrodes;

a tubing to deliver the mixed fluid into the two capillary electrodes, arranged in series and connected together through a delay tubing.

17. An analyzer comprising:

a hydraulic circuit which supplies a buffered sample liquid including a test substance for unidirectional travel through each of the following:
a first microcapillary flow-through electrode;
a reaction chamber;
a second microcapillary flow-through electrode;

wherein the reaction chamber comprises a tubing located between the first microcapillary flow-through electrode and the second microcapillary flow-through electrode, the tubing having a reactant immobilized on a wall of the tubing or confined within the tubing, whereby a reaction occurs in the reaction chamber involving the reactant and the test substance;

wherein output signals of the first microcapillary flow-through electrode and the second microcapillary flow-through electrode are used to determine a change in pH of the buffered sample liquid, the change in pH of the buffered sample liquid being indicative of the concentration of the test substance.

18. The apparatus of claim 17, wherein the reaction causes a change in hydrogen concentration of the buffered sample liquid.

* * * * *